United States Patent
Flesch et al.

(10) Patent No.: US 6,709,396 B2
(45) Date of Patent: Mar. 23, 2004

(54) ULTRASOUND ARRAY TRANSDUCER FOR CATHETER USE

(75) Inventors: Aimé Flesch, Andrésy (FR); Elisabeth Lacaze, Tournefeuille (FR); An Nguyen-Dinh, Valleres (FR); Philippe Auclair, Tours (FR); Rémi Dufait, Tours (FR); Pascal Mauchamp, Fondettes (FR)

(73) Assignee: Vermon, Tours Cedex (FR)

( * ) Notice: Subject to any disclaimer, the term of this patent is extended or adjusted under 35 U.S.C. 154(b) by 0 days.

(21) Appl. No.: 10/196,561

(22) Filed: Jul. 17, 2002

(65) Prior Publication Data

US 2004/0015084 A1 Jan. 22, 2004

(51) Int. Cl.$^7$ .................................. A61B 8/14
(52) U.S. Cl. .................. 600/459; 29/25.35; 128/916
(58) Field of Search ................... 600/437, 462, 600/463, 439, 466, 373, 467, 440, 471, 424, 459; 29/25.35; 128/660.1, 916, 899

(56) References Cited

U.S. PATENT DOCUMENTS

| 3,938,502 A | | 2/1976 | Bom |
| 4,605,009 A | | 8/1986 | Pourcelot et al. |
| 5,054,492 A | * | 10/1991 | Scribner et al. ............ 600/463 |
| 5,291,893 A | | 3/1994 | Slayton |
| 5,297,553 A | * | 3/1994 | Sliwa et al. ................. 600/459 |
| 5,377,685 A | * | 1/1995 | Kazi et al. .................... 600/463 |
| 5,735,282 A | * | 4/1998 | Hossack ....................... 600/458 |
| 5,803,083 A | * | 9/1998 | Buck et al. .................... 600/439 |
| 5,848,969 A | * | 12/1998 | Panescu et al. .............. 600/462 |
| 6,078,831 A | * | 6/2000 | Belef et al. .................. 600/424 |
| 6,248,075 B1 | * | 6/2001 | McGee et al. ............... 600/463 |
| 2003/0073906 A1 | * | 4/2003 | Flesch et al. ................ 600/459 |

FOREIGN PATENT DOCUMENTS

| WO | WO 92/03972 | 3/1992 |
| WO | WO 98/33430 | 6/1998 |

* cited by examiner

*Primary Examiner*—Dennis W. Ruhl
*Assistant Examiner*—Ruby Jain
(74) *Attorney, Agent, or Firm*—Stites & Harbison, PLLC; Ross F. Hunt, Jr.

(57) ABSTRACT

A catheter-based ultrasonic transducer array is provided which includes a piezoelectric member sandwiched between matching layers and a backing member. A flexible stiffening element or elements is embedded in the backing member. The element is opaque to radio frequencies and integrated along the azimuthal axis of the array so as to enable a user to view the element in an image of the array derived from the array output and thus determine the angular position of the array. A flexible interconnection assembly provides an electrical connection between the electrodes of the piezoelectric member and external cabling. Different methods are provided for adding a surrounding protective cover to the array.

14 Claims, 9 Drawing Sheets

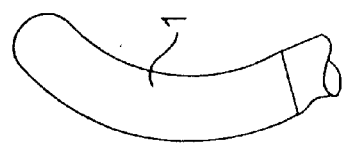
FIG. 11(a) -90°
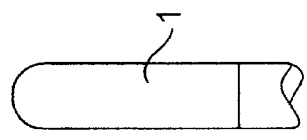
FIG. 11(b) 0°
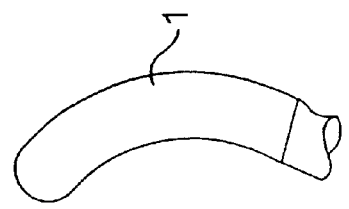
FIG. 11(c) +90°
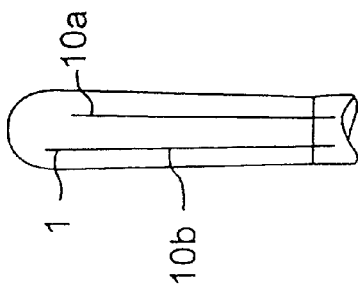
FIG. 12(a) -180°
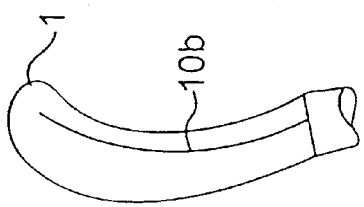
FIG. 12(b) -90°
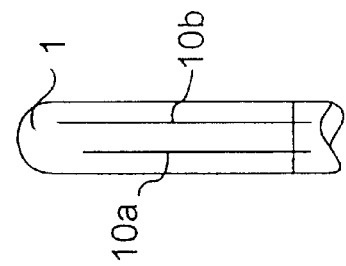
FIG. 12(c) 0°
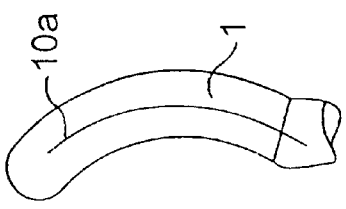
FIG. 12(d) +90°
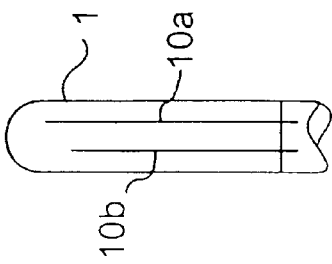
FIG. 12(e) +180°

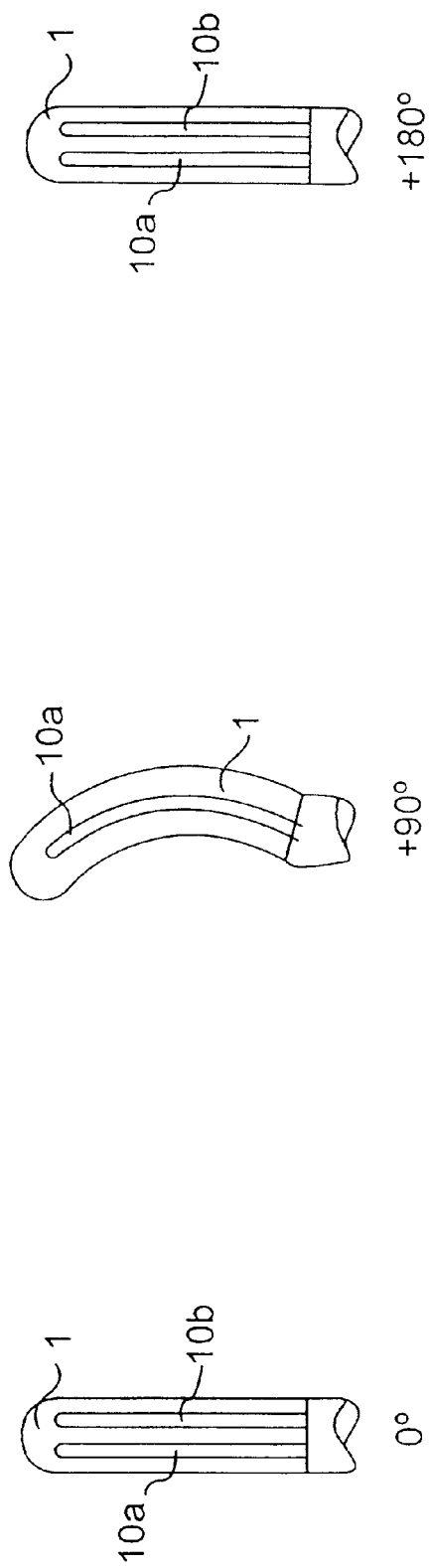
FIG. 13(a)  -180°
FIG. 13(b)  -90°
FIG. 13(c)  0°
FIG. 13(d)  +90°
FIG. 13(e)  +180°

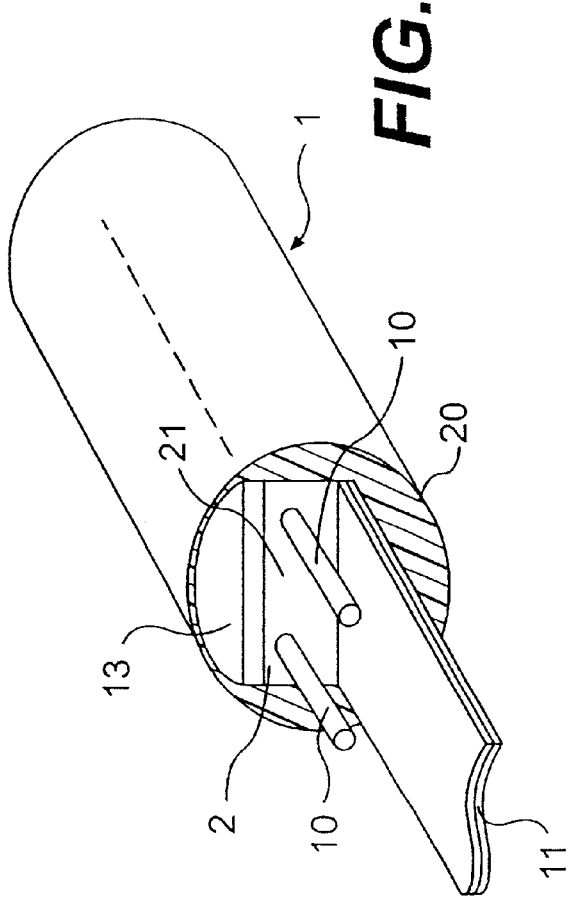
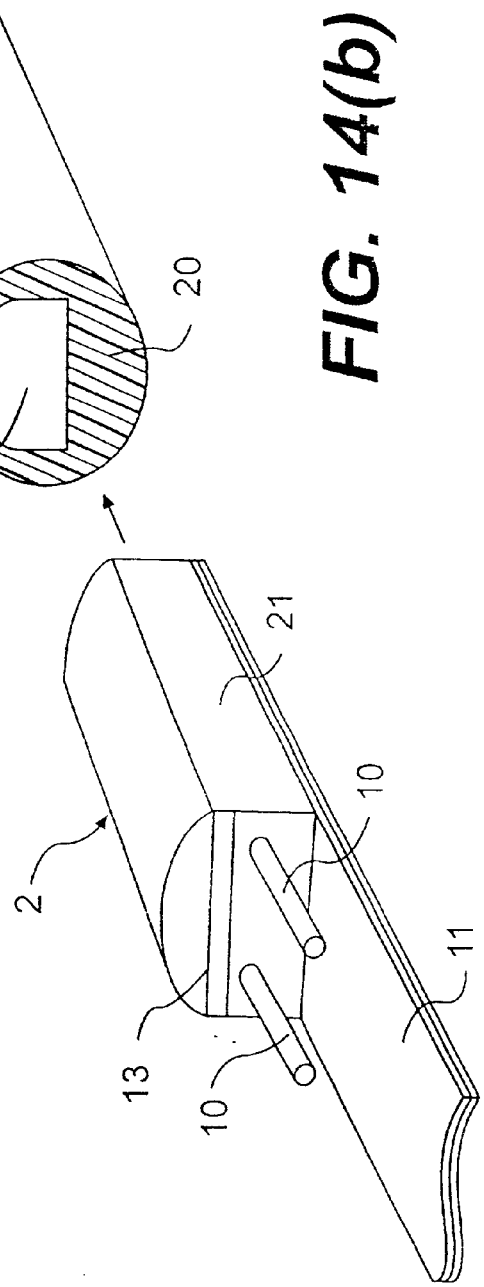
FIG. 14(a)
FIG. 14(b)

ULTRASOUND ARRAY TRANSDUCER FOR CATHETER USE

BACKGROUND OF THE INVENTION

1. Field of the Invention

The invention relates to an ultrasonic linear array transducer for utilization in catheter instruments and to methods of manufacturing curved linear array transducers for catheter-mounted applications so as to comply with acoustic and surgical specifications relating to such products.

2. Related Art

Intraluminal catheter-mounted ultrasonic transducers of several different kinds and forms have been widely discussed in the literature. Usually, the transducing device is attached at, or in the vicinity of, the tip end of the catheter, and wave radiation is then directed outwardly from the catheter either in a transverse radial mode, longitudinal radial mode, forwardly directed mode, circular radial mode or a combination thereof. The catheter instrument is basically comprised of an elongated tube having, at one end thereof, an insertion tip wherein the transducer is mounted and terminated at the other end by a handle wherein are gathered the bending controls for the instrument. Catheters designed for use in cardiac examinations commonly have a diameter ranging from 3 to 10 French catheter scale, meaning that the external diameter of the inserting tube does not exceed a value of, respectively, 1 to 3.3 mm. The tube is approximately of 1 to 2 meters long and is connected to the imaging transducer of the system by a flexible coupler which is capable of causing bending of the transducer tip in two or four directions.

An example of an imaging catheter is disclosed by U.S. Pat. No. 3,938,502 to Bom, wherein the catheter is a circular radially emitting device. The elements of the transducer array are disposed around the catheter circumference to form a circular scanning image. Such product is particularly well suited to arterial applications and more specifically, to examining for arteriosclerosis in plaque wherein a sectional view of the artery is required.

In U.S. Pat. No. 4,605,009 to Pourcelot, there is disclosed an endoscope probe for imaging an internal wall of human body. In order to widen the angle of view of the instrument, a curved linear array transducer is associated with optical visualization means. Assembly of the transducer includes the provision of a wire interconnection between the transducer piezoelectric member and a rigid printed circuit board (PCB) located at the bottom side of the transducer, and soldering of coaxial cables to the PCB to complete the interconnection. Such a construction is voluminous and prohibitive of any miniaturization of transducer for implementation thereof in intraluminal probes.

Another endoscopic ultrasonic instrument of interest is disclosed in U.S. Pat. No. 5,291,893 to Slayton wherein a linear array transducer is provided at the distal end of an endoscope or catheter. The transducer array is mounted in a tip housing that is capable of rotating around its longitudinal axis thereby providing rotation of the scanning plane without moving the catheter. However, the transducer array construction method includes the provision of an interconnection PCB located beneath the transducer assembly where coaxial cables and piezoelectric contact wires are soldered. Making the interconnection in this way wastes the considerable space behind the array so miniaturization of transducer tip diameter is difficult and the result unreliable. Furthermore, the rotation of the transducer tip with regard to the rest of the catheter requires a dynamic seal at the junction between the two moving parts. This junction is a collection site for dust accumulation and biological contamination so the device can not be reused in surgical operations. Further, with regard to the manufacturing cost of the device, there is no corresponding disposable diagnostic instrument available on the market.

PCT Patent WO92/03972 to Crowley relates to an imaging system combined with an insonifier for detecting the position and orientation of the associated catheter device. The insonifier utilizes ultrasound with a frequency that can be detected by the catheter sensor. The energy transferred between the insonifier and the catheter is maximized when the two devices face each other, so that by identifying the orientation of one of the devices, the position of either can be determined. Because the frequency of transmit energy from the insonifier should be at least in the bandwidth of catheter device, the separation distance between the two devices is limited. The external insonifier, when used as described in the patent, is difficult to control and in actual practice, the alignment of the insonifier relative to the catheter remains approximate.

In PCT Patent WO98/33430 to Curley, there is disclosed a catheter-mounted transducer array for ultrasonic imaging. The transducer includes an end portion surrounding the array and providing a speed of sound therein greater than or equal to 1250 ms$^{-1}$. The transducer azimuth axis is parallel to the longitudinal axis of the catheter and is molded or sheathed to have an elongated cylindrical tip portion having the same proportions as those of the catheter. The Curley patent discloses two alternative methods of making surrounding material for the array transducer, viz., a molding method and a pre-formed thermoplastic material. The surrounding material is characterized by its cylindrical crosssection without regard to the elevation focus of the array. Accordingly, the speed of sound in the surrounding material must be close to that of the propagation medium so as not to modify the focus of transducer. Otherwise, no details as to the placement of the transducer in molding method are provided. The pre-formed sheathing method provides for the assembly of the transducer array into the pre-formed sheath using a glass tube associated with a mandrel and subsequent heating to eliminate air gaps between the transducer array and the polymer sheath. One of the important drawbacks of this method concerns the difficulty of the insertion of the transducer array into the polymer sheath without causing damage to the array due to pressure exerted thereon. Further, the heat applied to the polymer sheath to shrink the sheath onto the array will inherently transfer heat to the transducer array and this heat can depolarize the piezoelectric structure thereof. Another aspect of the Curley patent that is not clearly described concerns the angular orientation of the array in the case where the polymer sheath is provided with an acoustic window which is designed with a particular radius (concave or convex). It is evident, that with this arrangement, the position of the elevation plane of the array with regard to the geometry of lens is of critical importance.

SUMMARY OF THE INVENTION

In accordance with the invention, there is provided a novel method for making ultrasonic imaging transducer arrays for catheter use which enables implementation of curved or linear array shapes as well as provides for detection of the array orientation by a radio-opacity method described below. The method of the invention is also compatible with low cost fabrication requirements and thus finds application in the high volume disposable catheter market.

According to one aspect of the invention, a linear ultrasonic array transducer assembly is provided for intraluminal catheter use wherein a curved linear ultrasonic transducer array is mounted at or on the distal end of an elongated catheter so as to provide expanded viewing of an organ to be imaged.

Another aspect of the invention concerns the provision of an ultrasonic transducer array construction which provides optimized acoustic performance as well as compact sizing so as to be compatible with conventional vascular insertion techniques. The associated transducer comprises a sandwich of a piezoelectric member, backing block or member, matching layer, focusing lens and bonded interconnection means.

A further aspect of the invention concerns the flexibility of the transducer array. The flexibility provided enables the transducer array to bend slightly in order to facilitate insertion thereon when embodied as a curved linear array. The transducer array then recovers its initial shape once arriving at the desired site.

Yet another aspect of the invention concerns the integration of stiffening dorsal elements or "sticks" that provide elasticity to the transducer array during an insertion operation as well as other advantages.

Still another aspect of the invention concerns the provision of dorsal elements or "sticks" which are opaque to radio frequencies and can be viewed during the imaging process so as to enable the examiner to detect the orientation of the transducer array during placement and use thereof.

An additional aspect of the invention concerns the provision of a polymer sheath or covering over the transducer array. In one preferred method of this aspect or embodiment, the molding of the polymer sheath is omitted and the transducer array is inserted into the tube of the catheter. The tube terminates in a flexible portion at which the array is located. Expansion of a flexible array receiving portion of the tube is provided in order to facilitate insertion of the transducer array into this flexible tube portion without excessive constraining forces being exerted thereon.

Further features and advantages of the present invention will be set forth in, or apparent from, the detailed description of preferred embodiments thereof which follows.

BRIEF DESCRIPTION OF THE DRAWINGS

FIGS. 11(a) to 11(c) are top plan views used in explanation of a method for detecting the position of a curved array transducer in the body of a patient through the use of angiography visualization;

FIGS. 12(a) to 12(e) are top plan views (angiographic views) of a transducer tip as equipped in accordance with a further embodiment so as to enable angular position detection;

FIGS. 13(a) to 13(e) are top plan views (angiographic views) of a transducer tip as equipped in accordance with yet another embodiment so as to enable angular position detection;

FIGS. 14(a) and 14(b) are perspective views of a profiled protective tube or protective cover showing a transducer assembly inserted therein and showing tube and assembly prior to such insertion, respectively;

DETAILED DESCRIPTION OF THE PREFERRED EMBODIMENTS

Figure 1:
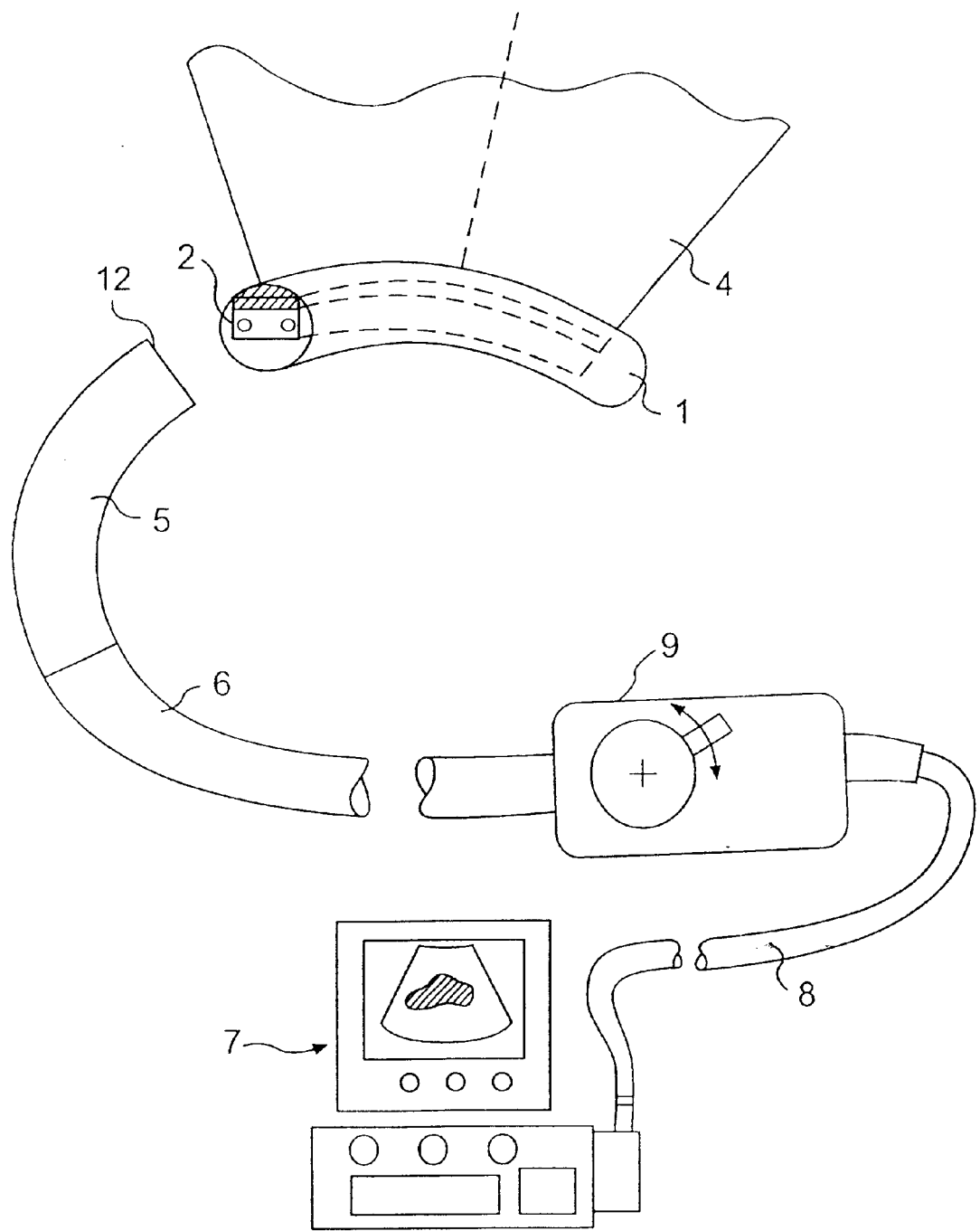
FIG. 1 is a schematic plan view of an ultrasonic catheter system including a perspective view, partially in cross section, of a curved linear transducer array of the catheter system.

Referring to FIG. 1, there is shown an ultrasonic transducer array 2 for catheter applications. The transducer array is particularly designed to match the diameter of the cardiac 9–10 French catheter scale (FCS). However, the device can be adapted for use with other diameters, even a 1 mm catheter (FCS 3).

In accordance with common practice, an imaging cardiac catheter is generally comprised of a flexible tube or tubing 6 of about 1–2 meters in length. Tube 6 is terminated by a transducer tip 1 which is attached to the distal end of the tube 6 by the intermediate of a bendable coupler 5, although coupler 5 is optional. Unlike the bendable couplers designed for reusable endoscopes, bendable couplers for catheters are of a very simple design to strictly limit the features thereof to the essential functionality, viz., bending. In most cases, the bendable coupler 5 would simply comprise a flexible tube portion equipped with one or two pairs of command cables which are adapted to slide along lumens disposed on the periphery of the flexible tube portion. This sliding action of one of the command cables will result in bending of the tube portion on the side thereof where the corresponding cable is located.

At the distal extremity of the bendable coupler 5, a transducer tip 1 is mounted. The interconnection means for the associated imaging transducer 2 pass through the central hollow space within the bendable coupler 5 so as to extend to the main tube of catheter and are then connected to an external coaxial cable 8 adapted to be plugged into an imaging system 7. All of the interconnection means for the external cables and command cables are commonly gathered together in a handle 9 of the probe device which is usually a separation point between disposable and reusable parts of the device. A more specific description of endoscope constructions of this type can be found, for example, in U.S. Pat. No. 5,681,263 to Flesch.

Figure 2:
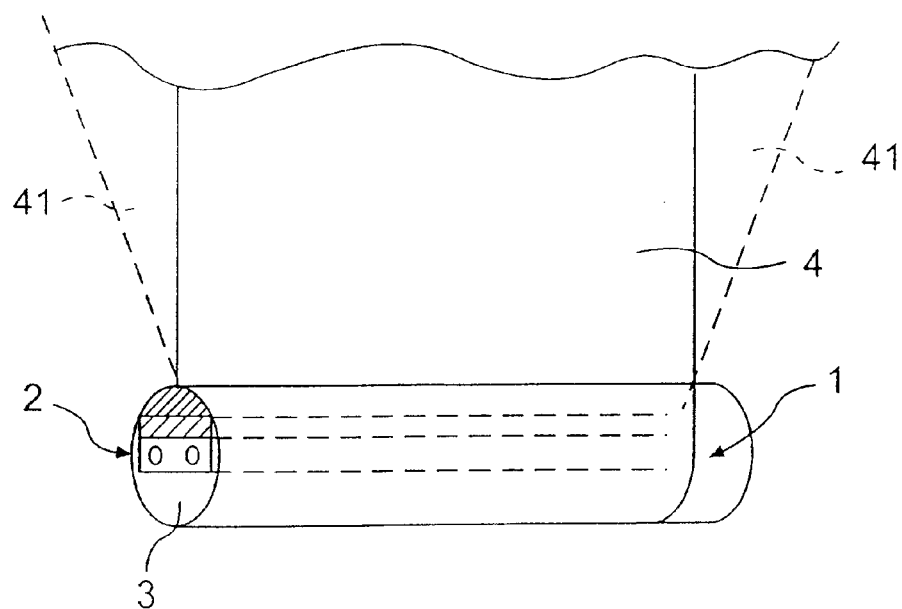
FIG. 2 is a perspective view, partially in cross section, of a linear transducer array for catheter use.

FIGS. 1 and 2 respectively show curved and linear array transducer shapes suited for catheter applications. However, the description of a preferred embodiment here will focus on the curved array ultrasonic transducer shown in FIG. 1. The transducer tip 1 is preferably of an elongated shape with a curvature in the azimuthal plan of the transducer 2. Because the transducer array 2 is driven by electronic phase shift beamformer (not shown) and is based on the curvature of the emitting surface, the insonified paths will define a sector angle indicated at 4 which represents the scanning area of the probe.

Referring to FIG. 2, in a similar manner, the scanning area 4 of the probe of FIG. 2 is generally in the shape of a rectangular section as shown in solid lines. However, sophisticated electronic beamformer techniques can be used to produce a sector shape scanning area 41, even if a linear array is used, by steering the acoustic beam with a predetermined angle when arriving at the extremity of array. It is noted that the image quality is somewhat deteriorated in this area but the user is still provided with specific features that only a curved or phased array can provide.

Returning to FIG. 1, the catheter assembly also comprises a shoulder portion 12 which is designed to interfit with the associated mounting part located at the distal end of bendable coupler 5.

As will be understood by those skilled in the art, the term transducer array is used here to designate all types of transducer arrays that comprise elementary transducers aligned in one direction in azimuth, and thus this term includes linear, curved and phased arrays.

Figure 3:
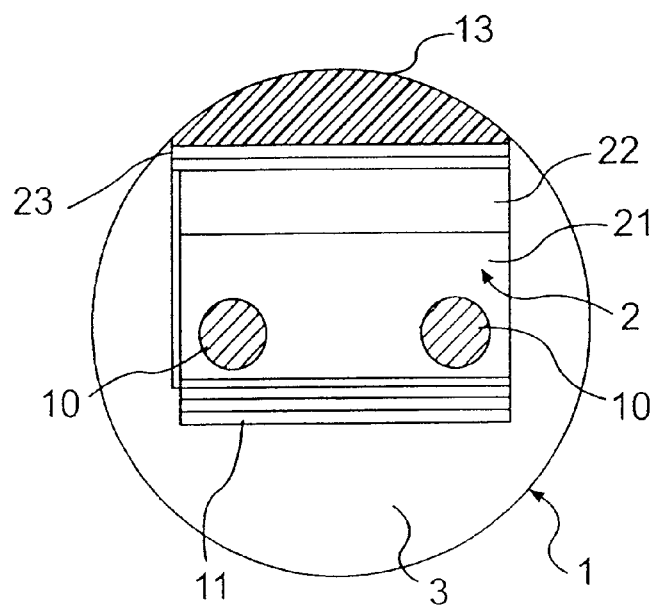
FIG. 3 is a more detailed cross sectional view of the transducer array of the catheter system of FIGS. 1 and 2.

FIG. 3 shows a cross sectional view of a transducer tip according to a preferred embodiment. As illustrated, the transducer assembly 2 is disposed in the top portion of the transducer tip 1 and comprises a piezoelectric member 22 sandwiched between one or more matching layers 23 and a backing member 21. The front face of the transducer 2 is preferably covered by an acoustic focusing lens 13 which is advantageously made of an elastomeric rubber providing a sound velocity therein lower than that of the propagation medium, such as the silicon rubbers TSE 3331 from GE Silicones, NY, USA. The backing member 21 includes a set of parallel spring elements or sticks 10 that are disposed alongside each other and located at or near the rear or bottom side of the backing member 21.

Figure 4:
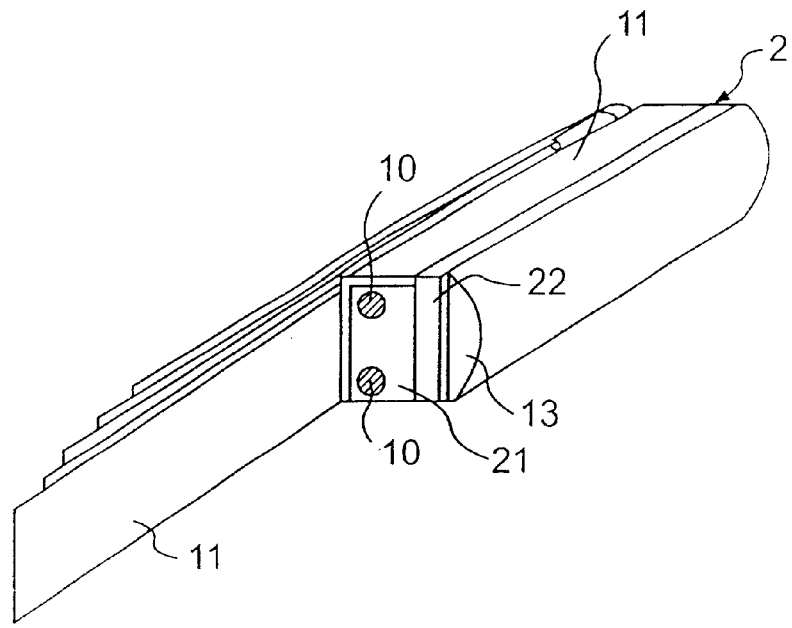
FIG. 4 is a perspective view of the transducer array of FIG. 3, as equipped with a flexible interconnection assembly.

A flexible printed circuit 11 is bonded to the rear electrode (not shown) of the piezoelectric member 22 through connecting portion as described below and folded to assume a longitudinal shape as shown in FIG. 4.

The transducer assembly 2 is embedded in a protective covering or molding 3 which is made of a suitable resin or polymer material and which is of a circular cross section to match the diameter of the catheter. Polymers that are compatible with the use thereof as the embedding molding 3 may be selected from the group consisting of polyurethanes, silicones, and polyether block amides resins (such as Pebax, Registered Trademark) and flexible epoxies. The molding method of mounting transducer assembly 2 is desirable in order to obtain a reliable and cosmetically finished device. However, other methods for obtaining an embedded transducer tip include, for example, a bonding of a finished transducer assembly into a pre-formed protective tip cover.

To provide a better understanding of the method of manufacturing of an imaging catheter transducer tip according to the preferred embodiment of the invention, reference will now be made to FIGS. 4 to 10. The method of manufacturing disclosed herein is particularly adapted to a small cross section transducer array and affords low cost fabrication.

Figure 5:
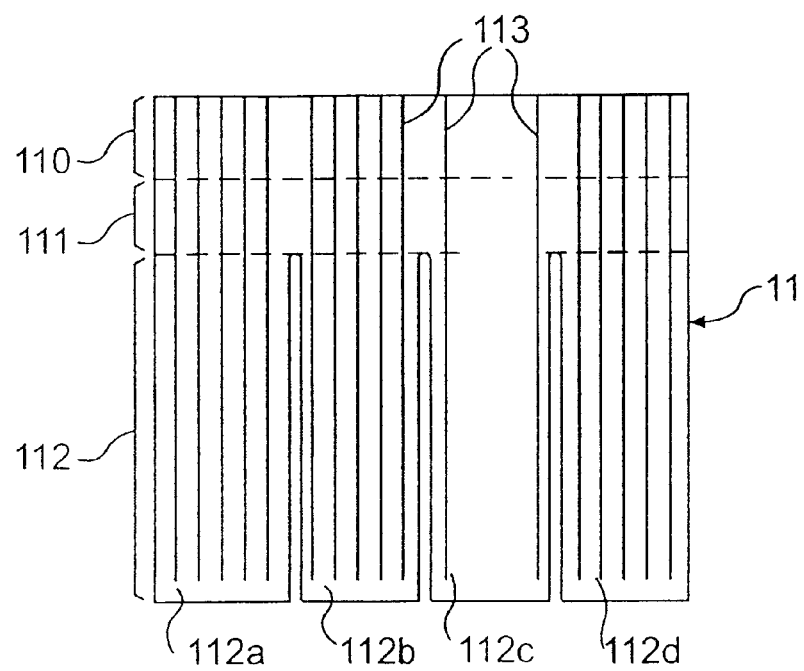
FIG. 5 is a front view of the flexible interconnection assembly of FIG. 4, in accordance with a preferred embodiment.
Figure 6:
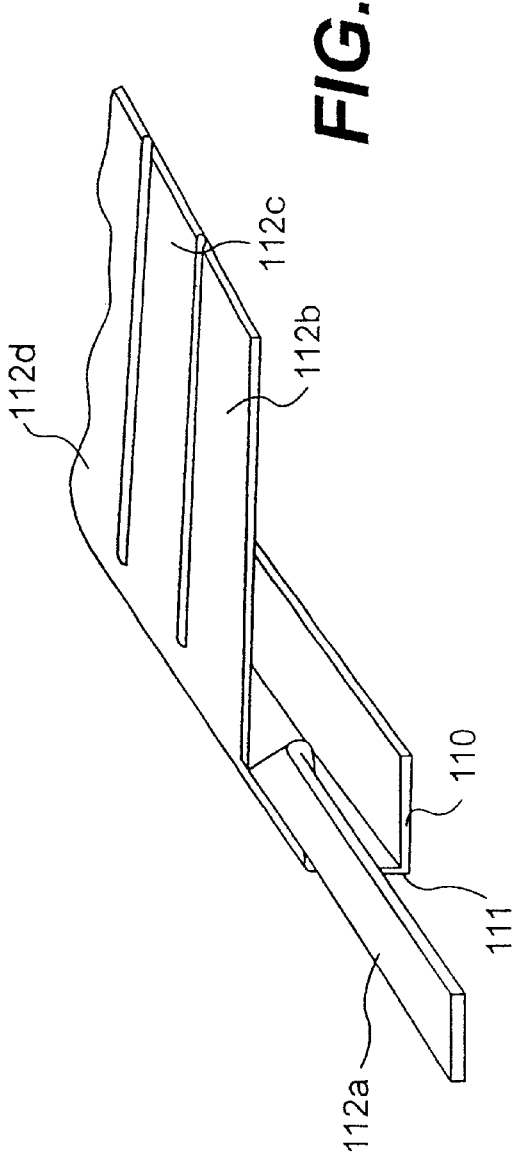
FIG. 6 is a perspective view of a preferred method of folding the flexible interconnection assembly of FIGS. 4 and 5 so as to achieve a compact device.

In the embodiment shown in FIGS. 4, 5 and 6, a particular aspect of the management of the flexible circuit 11 is provided. The flexible circuit 11, which is shown in planar shape in FIG. 5, is preferably of a single face design wherein conductive traces 113 are plated on a polyamide film of a thickness of 5 to 25 $\mu$m. The opposite face or surface of the film can be covered by a metal sheet or layer (not shown) in order to control the characteristic impedance of the conductive traces 113. Further, this metal layer provides interference protection with respect to electrical signals travelling through the conductive traces 113.

In this embodiment, the flexible circuit 11 is of a rectangular shape and has a first top or upper portion 110 which includes regularly spaced traces 113 having a pitch equal to that of the array of transducer. The conductive traces 113 of this first portion 110 are free of a cover layer or protective layer. The width of the portion 110 is equal to or smaller than that of the transducer elevation.

A second portion 111 of the flexible circuit 11 is located at the middle area of the circuit 11 and may be protected by cover layer if desired. The rest of the flexible circuit 11 constitutes a third portion 112 of the circuit 11. The third portion 112 of circuit 11 is divided longitudinally into strips 112a to 112d of equivalent length. It is noted that although four strips are illustrated, there is no limitation on the number of strips comprising the third portion 112. In general, the number of strips is governed by the ratio of length to elevation of the array. The strips 112a to 112d are obtained by spaced cuts through the third portion 112 of the flexible circuit 11. The cutting operation is advantageously performed by laser cutting or by a die-cutting process. The distal extremities of strips 112a to 112d are terminated in non-protected, metal plated traces in a manner such as to receive, or to be assembled to, optionally provided extending cables.

In an alternative embodiment of flexible circuit 11, the flexible circuit 11 is provided with a single central portion 110, surrounded by opposed portions corresponding to portions 111 which are, in turn terminated by portions corresponding to portions 112 at which strips 112a to 112d are defined.

FIG. 6 is a perspective view of the flexible circuit 11 after being partially folded prior to being assembled to the transducer assembly (not shown in FIG. 6). Although for clarity of the illustration, the transducer assembly is not shown in FIG. 6, it will be understood that the folding of the circuit 11 illustrated creates a generally rectangular void formed by the portions 110 and 111 of the flexible circuit 11 in which the transducer assembly is received. FIG. 6 shows the first portion 110 positioned so as to be bonded to the rear surface of the piezoelectric member of the transducer assembly, and folded perpendicularly to the portion 111. Portion 112 is then folded the same way with regard to the portion 111 so as to be in parallel with the portion 110. Strip 112a is then folded at an angle of 45 degrees with respect to the orientation of traces 113 (not shown in FIG. 6) so the strip 112a is disposed along the azimuthal axis of the array. Next, the second strip 112b is similarly folded so as to be superimposed on first strip 112a and so on. At the completion of this operation, the transducer assembly will exhibit a longitudinal shape wherein the flexible circuit 11 occupies a minimum of space and is properly arranged on the rear face of transducer as shown in FIG. 4.

Referring again to FIGS. 1 and 3, as previously described, the piezoelectric member 22 is sandwiched between backing member 21 and matching layer 23. The piezoelectric member 22 can be a PZT ceramic, a relaxor based single crystal or a composite comprising a blend of piezoelectric and passive materials. The piezoelectric member 22 has electrodes (not shown) plated on its major opposite surfaces and one of the electrodes is divided into a plurality of individual electrodes corresponding to the transducer elements. For interference protection reasons, it is desirable to direct the ground electrode of the piezoelectric member 22 toward the propagation medium so that the spaced electrodes are positioned at the rear face of the transducer and then bonded to the flexible circuit 11. The bonding operation between the piezoelectric 22 and the flexible circuit 11 is carried out under pressure to avoid the formation of excessive leftover adhesive. This method also maintains the flexibility of the transducer assembly. Adhesives or glues of the families of epoxies or urethanes are suitable candidates for this operation.

To ensure maximizing of the transducer energy transfer function, the front face of the piezoelectric member 22 must be matched to the propagation medium through the addition of one or more matching layers 23 (as described above in connection with FIG. 3) having a suitable thickness defined by the following relation: $t=\lambda/4$. Another method for optimizing transmission lines employs a transformer as described by B. Bramham "A convenient transformer for matching coaxial lines" in Electronic Engineering (January, 1961) and D. Emerson in QST (1997). Further, the acoustic impedance of such a device is determined with respect to either standard transmission lines or using a polynomial formula proposed by Desilets. In accordance with the usual requirements, when two matching layers are employed, the first matching layer has an impedance higher than that of the second layer assembled thereto so as to be disposed outermost of the transducer assembly. Methods for manufacturing and designing matching layers are widely described in the literature and are disclosed, for example, in Kino "Acoustic Waves" or Anderson "Acoustic Transducer." Matching layers are advantageously obtained by the molding or mechanical grinding of resins or polymers. The piezoelectric 22 is then pressure bonded to the matching layer or layers 23 and the flexible circuit 11 to form an intermediate transducer assembly.

The backing member 21 of the transducer assembly 2, according to a preferred embodiment thereof, comprises a stiffening or reinforcing arrangement provided by a pair of parallel elongated elements or "sticks" 10 embedded in the thickness of backing member 21. As indicated above, FIG. 3 shows a cross sectional view of the transducer assembly 2 wherein the parallel elements 10 are located symmetrically with regard to the central longitudinal axis of the transducer. The parallel elements 10 are also referred to as "dorsal stiffening sticks."

Figure 7:
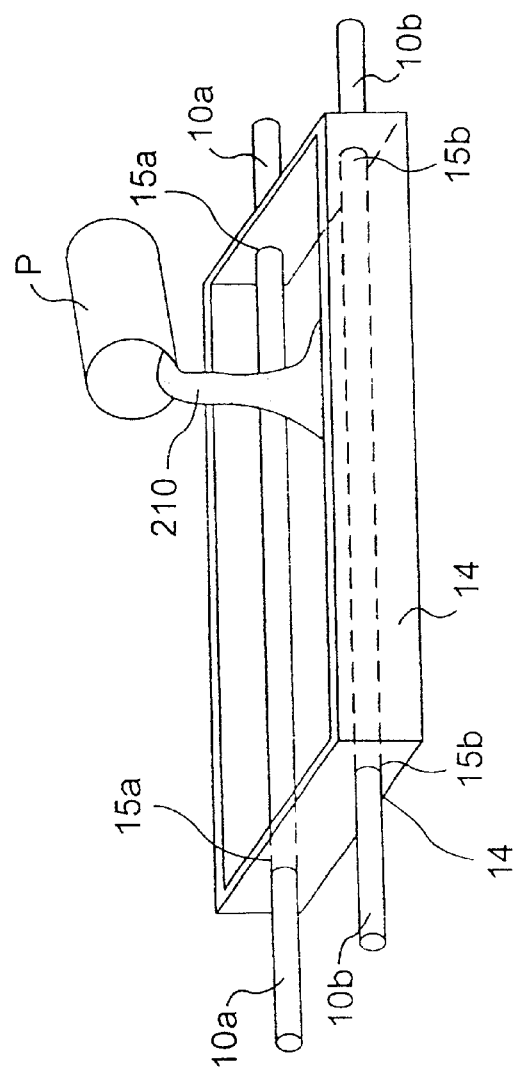
FIG. 7 is a perspective view of a step in a method of pre-formed fabrication of the dorsal element reinforced backing device of the array of FIG. 3.

Referring to FIG. 7, a step in a preferred method of manufacturing of the backing member 21 is shown. As illustrated, a rectangular shaped mold 14 is provided having two sets of openings 15a and 15b. The diameters of the openings 15a and 15b correspond to the diameters of the stiffening elements 10a and 10b. Stiffening elements or sticks 10a and 10b are preferably made of a spring material in order to provide flexibility to the backing member 21 if the latter is subjected to flexional forces but capable of recovering the initial shape or curvature thereof after removal of the force. Alloys such as NivaFlex® or Stainless steels (PrEN 10270-3) are suitable for this application.

It will be appreciated that in curved transducer array constructions, the mold for backing member 14 is curved as well, and the stiffening elements 10a and 10b will have the same curvature.

As shown in FIG. 7, resin 210 is poured from a pourer P into the mold 14 and hardening thereof ensues. In a "slim line" transducer construction according to the present invention, the backing material for backing member 21 is preferably selected from particle-filled attenuating resins such as Eccogel from Emerson&Cumings, and soft polyurethanes. Methods for obtaining highly attenuating materials are well known in the art and particles such as air filled plastic bubbles or air bubbles are used to provide the backing material with strong backscattering of incident wave propagation. Additionally, in case of linear or phased array transducers, the stiffening element backing member 21 can be made from a single long base member and individual backing members obtained by cutting the base member to desired lengths.

Figure 8:
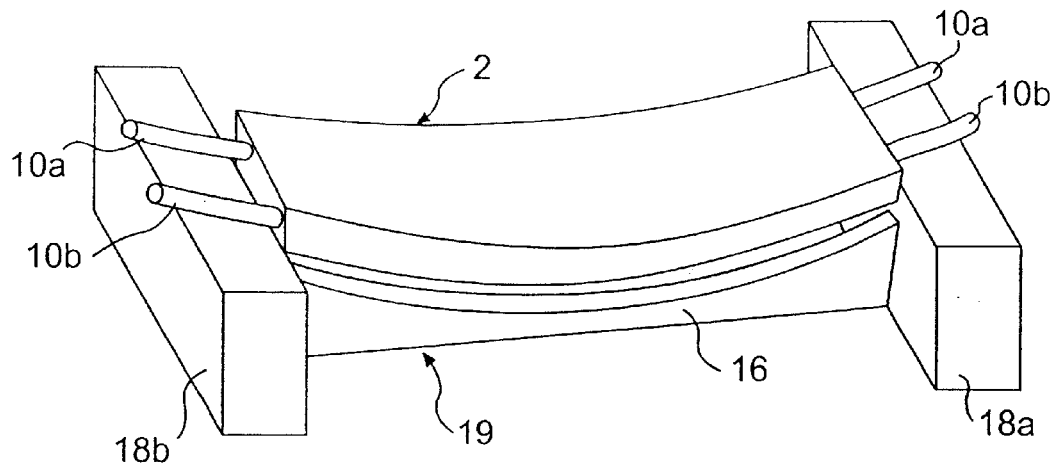
FIG. 8 is a perspective view of a tooling apparatus or molding tool for molding of the transducer tip of FIG. 3.
Figure 9:
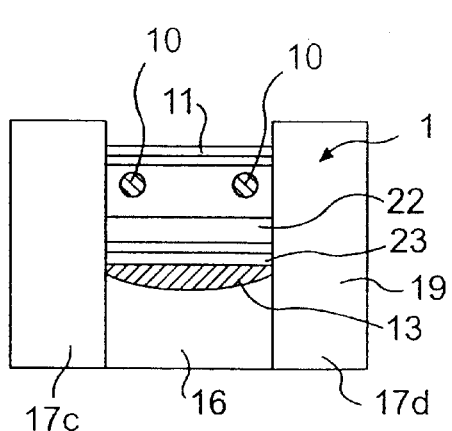
FIG. 9 is a cross sectional view of the molding tool of FIG. 8, as equipped with flat lateral "cheeks" for a lens molding operation.

FIGS. 8 and 9 depict a tooling apparatus for molding the transducer tip. Once the transducer assembly operation is complete, the transducer assembly 2 is disposed in a molding tool or mold 19. The mold 19 includes a dorsal carrier or member 16 which is designed to have a curvature corresponding to the curvature of the transducer assembly 2, if the assembly is curved. The dorsal carrier 16 is bounded at each extremity by plates 18a and 18b which are secured to the dorsal carrier 16 by a screw system, i.e., a plurality of screws. Care must be taken with respect to the geometry of the plate-dorsal carrier assembly in order to provide placement of the tooling apparatus within precise tolerances.

In this embodiment, the molding tool 19 is completed by adding two flat lateral cheeks or side members 17c and 17d to allow the molding of the focusing lens 13 described above in connection with FIG. 3. Because the carrier 16 has the same width as the transducer assembly, there should be no occurrence of excessive lens resin.

Figure 10:
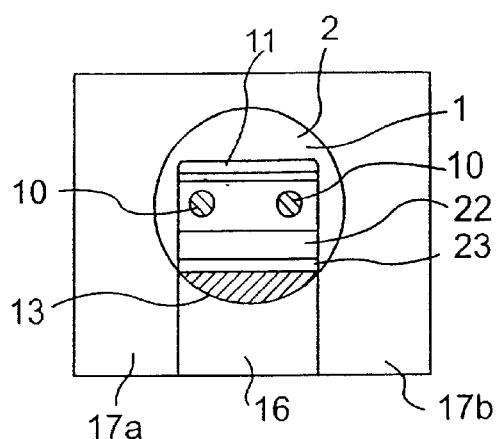
FIG. 10 is a cross sectional view of the molding tool of FIG. 8, as equipped with "dig cheeks" for a protective cover molding operation.

Once the lens material is cured, the lateral cheeks or side members 17c and 17d are then removed from tool 19 and will be replaced by further side mold members or "dig cheeks" 17a and 17b as shown in FIG. 10. As illustrated, cheeks 17a and 17b of FIG. 10 form a cylindrical hollow section with circular opening when cheeks 17a and 17b are coupled together. The hollow space formed is then filled with resin to obtain the protective cover 3 for the transducer 2, and thus, in doing so, determining the final diameter of the transducer tip 1. It is to be noted that the resin material used for lens 13 normally differs from that of protective cover 3. However, in a case where there is no particular specification with respect to transducer focus, the same resin can be used for both and so that only the step described in connection with FIG. 10 need be performed.

Another aspect of the cardiac catheter provided in accordance with the preferred embodiment of the invention concerns the ability to detect the orientation of the imaging transducer array 2 once inserted into an organ of the patient being treated. In practice, the catheter device is tracked and monitored using angiography X-ray imaging. During the insertion and use, the user is able to visualize the catheter tip in the body of the patient under X-ray ionization. However, when the transducer is of a linear elongate shape as opposed to a linear curved shape, no information is provided regarding the angular position of the transducer scanning plane, so that manual searching by the user of the image is required. When the transducer tip 1 is of a curved shape as shown, e.g., in FIG. 1, the X-ray images can provide a user with information regarding the transducer orientation by comparing the curvature of the transducer tip 1 with the images obtained. This is shown in FIGS. 11(a) to 11(c). For example, if the image is of a linear appearance as shown in FIG. 11(b), this means that that transducer scanning plane is aligned with ionizing source. On the other hand, an image having maximum curvature is obtained when the transducer scanning plane is rotated by 90° with respect to the ionizing source. Of course, the direction of the aligned scanning plane (0°) can only be specifically identified with rotation of the probe so that, for example, a left rotation of the catheter accompanied with appearance of a left convexity (−90°) as shown in FIG. 11(a) (i.e., a leftward facing convex curvature as viewed in the drawings) indicates that the front surface of the transducer is facing the ionizing source (oriented toward the ionizing source), whereas in the case of a left concavity (+90°) as shown in FIG. 11(c), the transducer is facing away from, and emitting in the same direction as, the ionizing source.

An alternative method for detecting the angular position of transducer tip is based on observation of the dorsal sticks or elements 10a, 10b embedded in the backing member 21 of the transducer assembly 2. Referring to FIGS. 12(a) to 12(e), in this embodiment, the transducer tip is provided with dorsal elements 10a and 10b of unequal length. As illustrated, element 10a is shorter than element 10b so that each cardinal (90°, 180°) angular position of the transducer array 2 can be recognized by observation of the appearance of the two elements 10a, 10b. FIGS. 12(a) to 12(e) show the relative positioning of the elements 10a, 10b for angular orientations of −180°, −90°, 0°, +90° and +180°, respectively. With this approach, a precise angular position adjustment can be facilitated.

Yet another method for determining or recognizing the angular position of the transducer tip is implemented with a set of dorsal elements 10a, 10b which are of same length but are of different diameters as shown in FIGS. 13(a) to 13(e). More specifically, in this embodiment, the set of elements or sticks comprises a first stick 10a having a first diameter and a second stick 10b having a second diameter significantly larger than the first diameter. When the transducer tip 1 is facing the ionizing source (0°), the two diameters are clearly distinguishable from the monitoring images and, moreover, at each cardinal position of the tip (90°, 180°), a particular image is obtained which differs from the others as shown in FIGS. 13(a) to 13(e), for the angles −180°, −90°, 0°, +90° and +180°, respectively. Accordingly, angular position can be determined in basically the same manner as previously described. Similarly, a hollow element or stick can be used, together with a standard element or stick, or a twisted stick together with a standard stick, can be also used, to provide similar positional information.

In a second embodiment of the invention, the basic transducer assembly remains unchanged. However, in order to reduce manufacturing cost of the device, the protective cover molding operation described above is omitted and replaced by the use of a pre-formed hollow tube having a hollow or internal cross section which corresponds to the cross section of the transducer assembly. In FIGS. 14(a) and 14(b), a portion of such a pre-formed profiled tube 20 is shown. Tube 20 can be obtained by cutting the tube from a continuously extruded or injection molded base tube. Suitable materials for tube 20 include materials selected from the group consisting of elastomeric rubbers such as Pebax, PU and the like. It is desirable to select materials having a sound velocity similar than that of biologic tissue in order to not disturb the focal geometry of the transducer. However, where there is a significant sound velocity difference, suitable compensation can be provided by adjustment of the radius of curvature of the lens 13.

The portion of tube 20 used to form cover 3, is cut to a length equal to that of the transducer assembly 2. As the base tube is obtained from extrusion molding process, the dimensions of a hollow section 23 are made to be somewhat smaller than those of the transducer assembly 2 so that once assembled together, the tube 20 will slightly bear on the external surface of assembly 2 so as to assure that perfect contact is provided between the covering tube 20 and the external surface of the transducer member 2.

Figure 16:
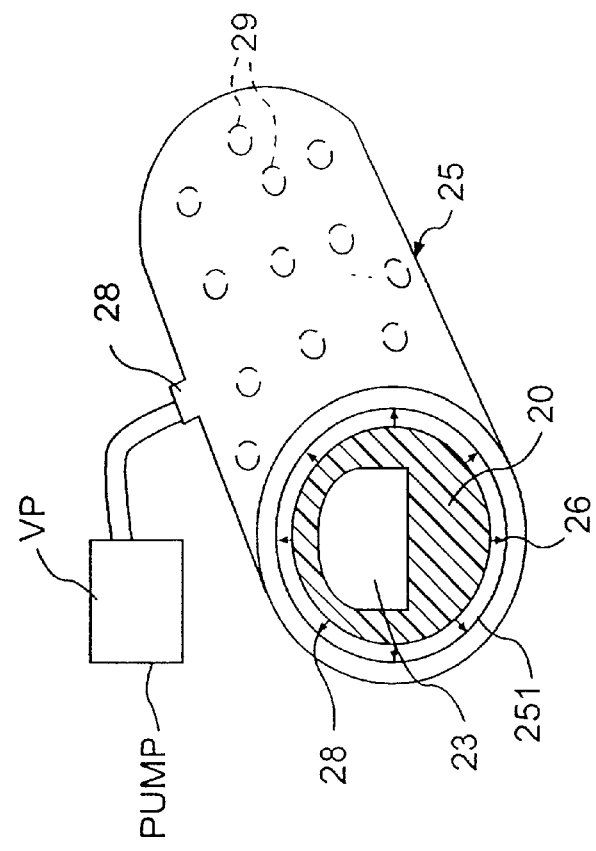
FIG. 16 is a perspective view of an inserting tool for the protective cover assembly, in accordance with a further embodiment.

As shown in FIG. 16, the insertion operation wherein transducer assembly 2 is inserted into tube 20 is advantageously achieved using a vacuum cylinder 25 that causes expanding of the diameter of tube 20 in such proportion as to permit the transducer assembly 2 to be inserted into tube 20 without the generation of excessive friction. As illustrated, the vacuum cylinder 25 is constructed with an internal volume 26 which communicates with a vacuum pump VP via an input conduit 28. The internal surface 251 of cylinder 25 is provided with a plurality of randomly distributed through holes 29 (shown in dashed lines) and cylinder 25 preferably has a diameter of 5% greater to that of the profiled tube 20. The cylinder 25 is closed at its two extremities by two end plates or lids (not shown) which thus define a central hollow space slightly smaller than the diameter of the profiled tube 20. In operation, the profiled tube 20 is placed in the cylinder 25 and the lids (not shown) are mounted at the extremities of cylinder, vacuum is then provided to the cylinder 25 from pump VP and the external surface of the profiled tube 20 is drawn outwardly so as to contact the surface 251. The hollow section or opening 23 of tube 20 is inherently caused to expand in size so that the transducer assembly 2 can then be inserted therein. Prior to inserting the transducer assembly 2, an adhesive, such as a suitable glue, is applied, preferably to the entire surface of the transducer assembly 2, in order to provide an air gap free assembly.

Figure 15:
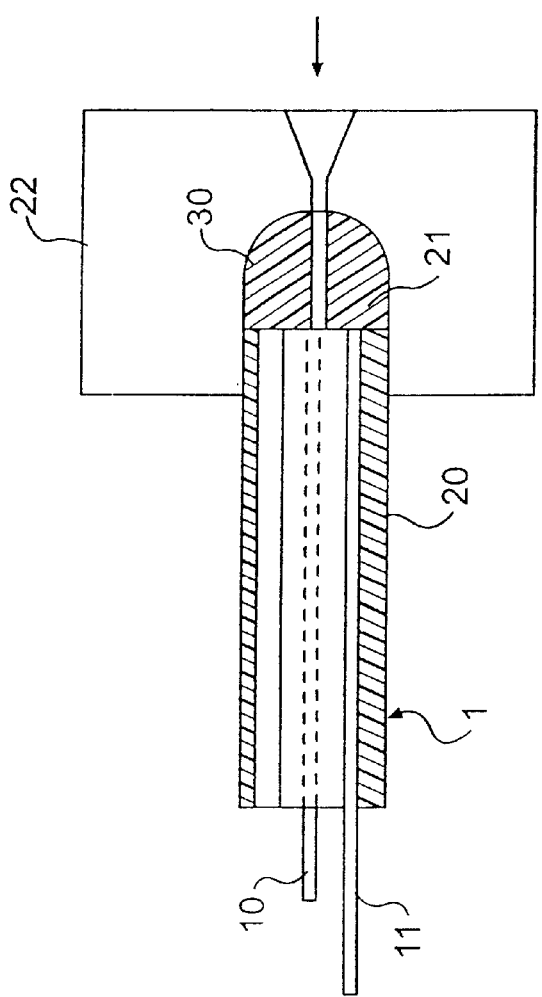
FIG. 15 is a perspective view of a step in a molding operation for the transducer end-tip.

FIG. 15 shows an end-tip molding operation where the transducer tip 1 is placed into mold 22 which has a hemispherically shaped opening 30 therein. Liquid resin 21 is injected into the opening 24 to fill the space between the transducer assembly 2 and the mold 22 to form the tip extremity of the transducer probe. This tip molding method is more suitable for high quantity production where the fabrication of profiled tube is contemplated. It is important to note that this method of making transducer protection cover is only feasible when applied to a transducer assembly with a perfectly constant cross section. Otherwise, the final product will exhibit an irregular external surface due to the constant thickness and flexibility of the protective cover portion.

Although the invention has been described above in relation to preferred embodiments thereof, it will be understood by those skilled in the art that variations and modifications can be effected in these preferred embodiments without departing from the scope and spirit of the invention.

What is claimed is:

1. A catheter-based ultrasonic transducer array assembly, said assembly comprising:
   at least one matching layer;
   a backing member;
   a piezoelectric member having electrodes and being sandwiched between the at least one matching layer and the backing member;
   at least one stiffening element disposed rearwardly of said piezoelectric member so as to provide stiffening of said assembly, said at least one stiffening element comprising a pair of elongate elements disposed in side by side relation;

flexible interconnection means for providing connection between the electrodes of the piezoelectric member and at least one external cable; and a surrounding protective cover.

2. A transducer array assembly as claimed in claim 1 wherein the at least one matching layer has a front face, said assembly further comprising a focusing lens attached to the front face of the at least one matching layer.

3. A transducer array assembly as claimed in claim 1 wherein said stiffening elements are of different lengths.

4. A transducer array assembly as claimed in claim 1 wherein said stiffening elements are of different thicknesses.

5. A transducer array assembly as claimed in claim 1 wherein the transducer assembly has an azimuthal axis and has, in use, an angular position, wherein an image of the transducer assembly is derived using imaging energy of predetermined wavelengths, and wherein said at least one stiffening element of said assembly comprises at least one element opaque to said predetermined wavelengths and oriented along the azimuthal axis of the transducer assembly to enable a user to view the at least one element in an image of the transducer assembly derived from an output of the transducer assembly and thus determine the angular position of the transducer assembly.

6. A transducer array assembly as claimed in claim 5 wherein said at least one element comprises a pair of elongate elements disposed in side by side relation.

7. A transducer array assembly as claimed in claim 6 wherein said elements are of different lengths.

8. A transducer array assembly as claimed in claim 6 wherein said elements are of different thicknesses.

9. A transducer array assembly as claimed in claim 1 wherein said at least one matching layer, said backing member, and said piezoelectric member form a transducer having a cross section, and said assembly further comprises an elastomeric tube, having an internal hollow space therein of a cross section corresponding to the cross section of the transducer, in which said transducer is disposed so as to form a transducer tip, one end of said transducer tip comprising a smooth tip extremity molded from a flexible resin.

10. A transducer array assembly as claimed in claim 1 wherein said electrodes include front and rear electrodes and said flexible connection means comprises a flexible circuit assembled to the rear electrodes of the piezoelectric member, said flexible circuit being folded along a lateral side of the backing member and said flexible circuit including flexible strips folded so as to provide superposition of the strips on a rear surface of the backing member.

11. A transducer array assembly as claimed in claim 1 wherein said transducer assembly undergoes different positioning in use and wherein said at least one stiffening member functions as an orientation marker for assisting in determining transducer assembly positioning.

12. An ultrasonic catheter device comprising:

an elongate tubular member having a distal end; and a transducer tip located at the distal end of the tubular member, said transducer tip undergoing different positioning in use and comprising a transducer assembly comprising:

at least one matching layer, a backing member;

a piezoelectric member having electrodes and being sandwiched between the at least one matching layer and the backing member;

at least one stiffening element of a predetermined shape located rearwardly of the piezoelectric member so as to function to provide stiffening of the transducer assembly and to further function as an orientation marker for assisting in determining the transducer tip positioning; and flexible interconnection means for providing connection between the electrodes of the piezoelectric member and at least one external cable.

13. A catheter device as claimed in claim 12 wherein said at least one stiffening element comprises a pair of elongate elements disposed in side by side relation.

14. A catheter device as claimed in claim 13 wherein said elongate elements are of different lengths.

* * * * *